US00PP35822P2

(12) United States Plant Patent
Sakazaki

(10) Patent No.: US PP35,822 P2
(45) Date of Patent: May 21, 2024

(54) ***CALIBRACHOA* PLANT NAMED 'WNCALSBDBLWH24'**

(50) Latin Name: ***Calibrachoa* sp.**
Varietal Denomination: WNCALSBDBLWH24

(71) Applicant: Ushio Sakazaki, Shiga (JP)

(72) Inventor: Ushio Sakazaki, Shiga (JP)

(73) Assignee: WINGEN, LLC, Mustang Ridge, TX (US)

( * ) Notice: Subject to any disclaimer, the term of this patent is extended or adjusted under 35 U.S.C. 154(b) by 0 days.

(21) Appl. No.: 18/237,633

(22) Filed: Aug. 24, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
*Assistant Examiner* — Zachariah Allan Kay
(74) *Attorney, Agent, or Firm* — C. Anne Whealy

(57) ABSTRACT

A new and distinct *Calibrachoa* plant named 'WNCALSBDBLWH24', characterized by its compact, upright to outwardly spreading and mounding to trailing plant habit; moderately vigorous growth habit; freely branching habit; dense and bushy appearance; early and freely flowering habit; double-type flowers with white-colored petals and petaloids; and excellent container and garden performance.

2 Drawing Sheets

Figure 1:
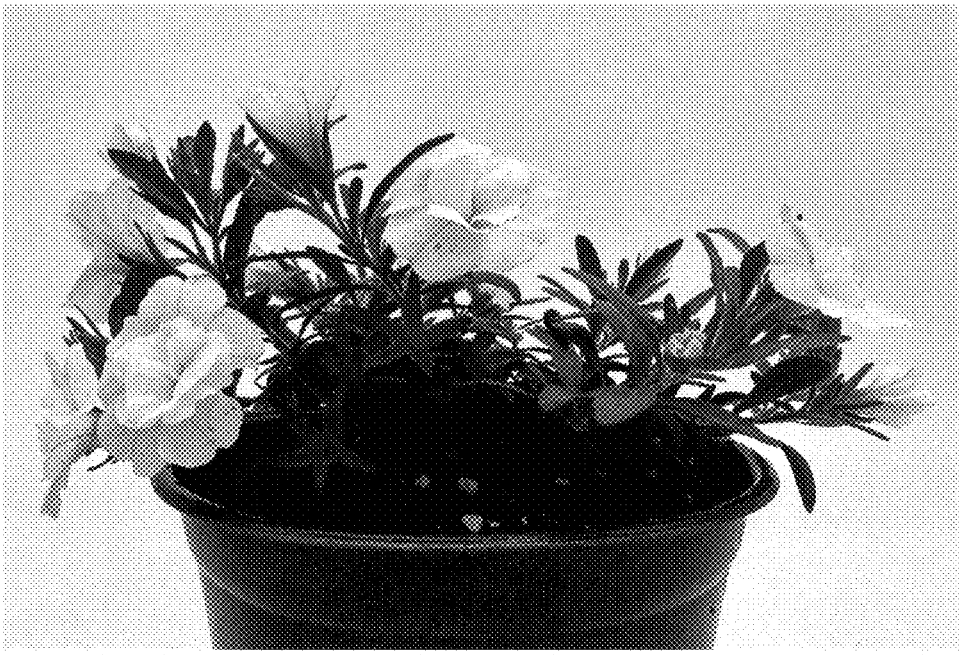

Botanical designation: *Calibrachoa* sp.
Cultivar denomination: 'WNCALSBDBLWH24'.

BACKGROUND OF THE INVENTION

The present invention relates to a new and distinct cultivar of *Calibrachoa* plant, botanically known as *Calibrachoa* sp. and hereinafter referred to by the name 'WNCALSBDBLWH24'.

The new *Calibrachoa* plant is a product of a planned breeding program conducted by the Inventor in Higashiomi, Shiga, Japan and Bonsall, California. The objective of the breeding program is to create new compact, uniform, freely-branching and freely-flowering *Calibrachoa* plants with attractive double-type flowers and good container and garden performance.

The new *Calibrachoa* plant originated from a cross-pollination conducted by the Inventor in Higashiomi, Shiga, Japan on May 25, 2018 of *Calibrachoa* sp. 'KLECA22893', not patented, as the female, or seed, parent with *Calibrachoa* sp. 'Million Bells Gran White', not patented, as the male, or pollen, parent. The new *Calibrachoa* plant was discovered and first selected by the Inventor as a single flowering plant within the progeny of the stated cross-pollination in a controlled greenhouse environment in Bonsall, California on Jul. 2, 2019.

Asexual reproduction of the new *Calibrachoa* plant by vegetative terminal cuttings in a controlled greenhouse environment in Bonsall, California since Jul. 8, 2019 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'WNCALSBDBLWH24'. These characteristics in combination distinguish 'WNCALSBDBLWH24' as a new and distinct *Calibrachoa* plant:

1. Compact, upright to outwardly spreading and mounding to trailing plant habit.
2. Moderately vigorous growth habit.
3. Freely branching habit; dense and bushy appearance.
4. Early and freely flowering habit.
5. Double-type flowers with white-colored petals and petaloids.
6. Excellent container and garden performance.

Plants of the new *Calibrachoa* differ primarily from plants of the female parent, 'KLECA22893', in the following characteristics:

1. Plants of the new *Calibrachoa* are more mounding than and not as trailing as plants of 'KLECA22893'.
2. Flower petals and petaloids of plants of the new *Calibrachoa* are pure white in color whereas flower petals and petaloids of plants of 'KLECA22893' are white in color with yellow-colored bases giving a yellowish flower center.

Plants of the new *Calibrachoa* differ primarily from plants of the male parent, 'Million Bells Gran White', in the following characteristics:

1. Plants of the new *Calibrachoa* flower earlier than plants of 'Million Bells Gran White'.
2. Flowers of plants of the new *Calibrachoa* are double-types whereas flowers of plants of 'Million Bells Gran White' are single-types.

Plants of the new *Calibrachoa* can be compared to plants of the *Calibrachoa* sp. 'USCAL51505', disclosed in U.S.

Plant Pat. No. 30,803. In side-by-side comparisons, plants of the new *Calibrachoa* differ primarily from plants of 'USCAL51505' in the following characteristics:

1. Plants of the new *Calibrachoa* are more mounding than and not as spreading and trailing as plants of 'USCAL51505'.
2. Plants of the new *Calibrachoa* are more compact than and not as vigorous as plants of 'USCAL51505'.
3. Flower petals and petaloids of plants of the new *Calibrachoa* are pure white in color whereas flower petals and petaloids of plants of 'USCAL51505' are pale yellow in color.

Plants of the new *Calibrachoa* can also be compared to plants of the *Calibrachoa* sp. 'BALCAL14141', disclosed in U.S. Plant Pat. No. 30,200. In side-by-side comparisons, plants of the new *Calibrachoa* differ primarily from plants of 'BALCAL14141' in the following characteristics:

1. Plants of the new *Calibrachoa* are more mounding than and not as upright as plants of 'BALCAL14141'.
2. Flowers of plants of the new *Calibrachoa* are double-types whereas flowers of plants of 'BALCAL14141' are single-types.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph on the first sheet (FIG. 1) is a side perspective view of a typical flowering plant of 'WNCALSBDBLWH24' grown in a container.

Figure 2:
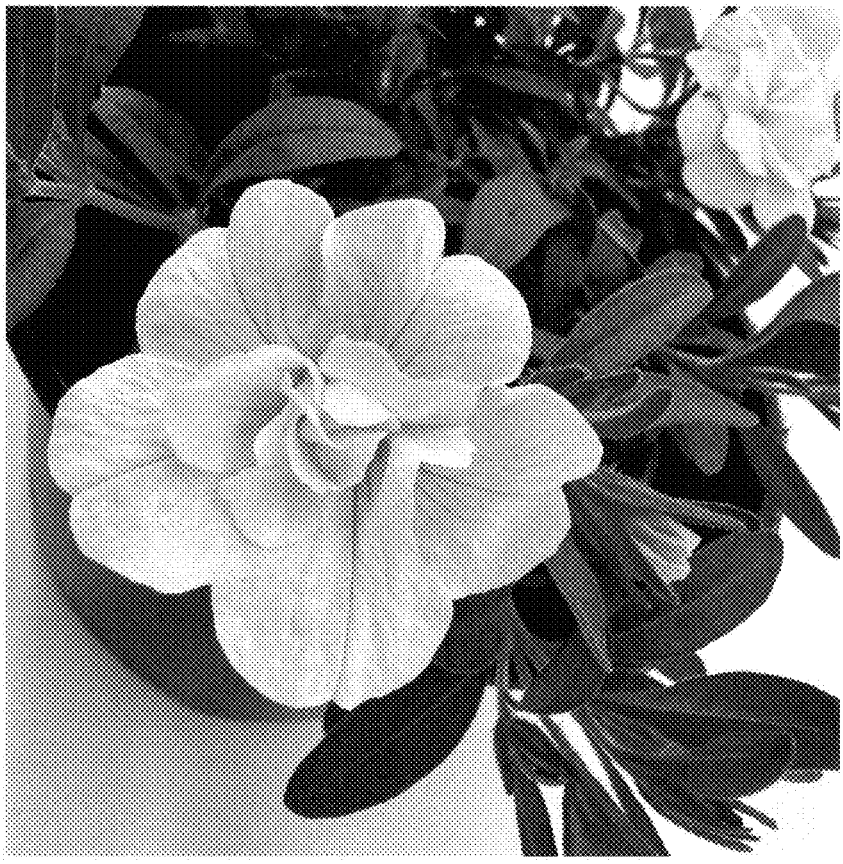

The photograph on the second sheet (FIG. 2) is a close-up view of a typical flowering plant of 'WNCALSBDBLWH24'.

DETAILED BOTANICAL DESCRIPTION

The aforementioned photographs and following observations and measurements describe plants grown during the spring in 723-ml containers in a glass-covered greenhouse in Loudon, New Hampshire and under cultural practices typical of commercial *Calibrachoa* production. During the production of the plants, day and night temperatures averaged 20C. Plants were seven weeks from planting rooted cuttings when the photographs and description were taken. In the following description, color references are made to The Royal Horticultural Society Colour Chart, 2015 Edition, except where general terms of ordinary dictionary significance are used.

Botanical classification: *Calibrachoa* sp. 'WNCALSBDBLWH24'.

Parentage:

*Female, or seed, parent.*—*Calibrachoa* sp. 'KLECA22893', not patented.

*Male, or pollen, parent.*—*Calibrachoa* sp. 'Million Bells Gran White', not patented.

Propagation:

*Type.*—By vegetative terminal cuttings.

*Time to initiate roots, summer.*—About five to seven days at ambient temperatures about 28C.

*Time to initiate roots, winter.*—About seven to ten days at ambient temperatures about 20C.

*Time to produce a rooted plant, summer.*—About four to five weeks at ambient temperatures about 28C.

*Time to produce a rooted plant, winter.*—About five to six weeks at ambient temperatures about 20C.

*Root description.*—Fine, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding to eventually trailing plant habit; freely branching habit with about six to eight primary lateral branches with secondary laterals developing potentially at every node, dense and bushy plant form; pinching enhances development of lateral branches; moderately vigorous growth habit and rapid growth rate.

*Plant height.*—About 12 cm.

*Plant diameter.*—About 27 cm by 31 cm.

Lateral branch description:

*Length.*—About 12 cm.

*Diameter.*—About 2 mm.

*Internode length.*—About 1.7 cm.

*Strength.*—Moderately strong, flexible and sturdy.

*Aspect.*—About 45 to 60 degrees from stem axis.

*Texture and luster.*—Densely pubescent; pubescence, minute; matte to slightly glossy.

*Color, developing.*—Close to 144A.

*Color, developed.*—Close to 144A.

Leaf description:

*Arrangement.*—Alternate, simple.

*Length.*—About 3.2 cm.

*Width.*—About 1.1 cm.

*Shape.*—Narrowly elliptic.

*Apex.*—Broadly acute to rounded.

*Base.*—Attenuate.

*Margin.*—Entire.

*Texture and luster, upper and lower surfaces.*—Sparsely to moderately pubescent; pubescence, minute; matte to slightly glossy.

*Venation pattern.*—Pinnate; arcuate.

*Color.*—Developing leaves, upper surface: Close to 146A. Developing leaves, lower surface: Close to 146A. Fully expanded leaves, upper surface: Close to between NN137A and 147A; midvein, close to 146A and lateral venation, close to between NN137A and 147A. Fully expanded leaves, lower surface: Close to 146A; venation, close to 146A.

*Petioles.*—Length: About 7.5 mm. Diameter: About 1.5 mm. Strength: Moderately strong, flexible. Texture and luster, upper and lower surfaces: Moderately pubescent; pubescence, minute; matte to slightly glossy. Color, upper and lower surfaces: Close to 146A.

Flower description:

*Flower type and flowering habit.*—Double-type flowers arising from leaf axils; freely flowering habit with typically about 60 to 70 flowers and flower buds developing per plant at one time; flowers face upright to mostly outwardly.

*Fragrance.*—None detected.

*Natural flowering season.*—Plants of the new *Calibrachoa* begin flowering about five weeks after planting; plants flower continuously from the spring though the summer until frost.

*Flower longevity.*—Depending on temperature, about one to two weeks; flowers persistent.

*Flower buds, before showing petal color.*—Length: About 1.1 cm. Diameter: About 4 mm. Shape: Oblong, elongate. Texture and luster: Sparsely to moderately pubescent; pubescence, minute; matte. Color: Close to 146A.

*Flower diameter.*—About 4.1 cm.

*Flower length (height).*—About 2.4 cm.

*Flower tube length.*—About 1.75 cm.

*Flower tube diameter, proximally.*—About 2 mm.

*Corolla.*—Arrangement: Five petals in a single whorl with five to six petaloids in one to two whorls. Petal length: About 1.9 cm. Petal width: About 2 cm. Petaloid length (largest petaloids): About 1.7 cm. Petaloid width (largest petaloids): About 1.5 cm. Petal and petaloid shape: Fan-shaped with cordate tendencies. Petal and petaloid apex: Emarginate. Petal and petaloid margin: Entire; slightly undulate. Petal and petaloid texture and luster, upper surface: Smooth, glabrous; velvety; matte. Petal and petaloid texture and luster, lower surface: Smooth, glabrous; slightly glossy. Tube texture and luster: Moderately pubescent; matte. Color, petals and petaloids: When opening, upper and lower surfaces: Close to NN155D. Fully opened, upper and lower surfaces: Close to NN155D; at the base of the petaloids, close to N144A; venation, close to 144A to 144B; color does not change with subsequent development. Tube: Close to 4C to 4D; venation, close to 144A.

*Calyx.*—Arrangement: One star-shaped calyx tube with five sepals fused towards the base and arranged in a single whorl; sepals flaring outwardly and reflexing towards the apex. Length: About 1.5 cm to 1.75 cm. Diameter: About 5 mm. Sepal length: About 1.5 cm to 1.75 cm. Sepal width: About 3.5 mm. Sepal shape: Narrowly lanceolate. Sepal apex: Acute. Sepal margin: Entire. Sepal texture and luster, upper and lower surfaces: Moderately pubescent; pubescence, minute; matte. Sepal color, upper and lower surfaces: Close to 146A.

*Peduncles.*—Length: About 1.5 cm to 1.9 cm. Diameter: About 1.5 mm. Angle: About 45 to 70 degrees from stem axis. Strength: Moderately strong, wiry and flexible. Texture and luster: Moderately pubescent; pubescence, minute; matte. Color: Close to 146A.

*Reproductive organs.*—Stamens: No stamens observed, all fully transformed into petaloids. Pistils: Quantity: One per flower. Pistil length: About 9 mm. Style length: About 6 mm. Style color: Close to 146C. Stigma diameter: About 1 mm. Stigma shape: Round. Stigma color: Close to 148A tinged with close to 187A. Ovary color: Close to 144A.

*Seeds and fruits.*—To date, seed and fruit development have not been observed on plants of the new *Calibrachoa.*

Garden performance: Plants of the new Petunia have been observed to have excellent garden performance and have been observed to tolerate rain, wind and temperatures ranging from about 1C to about 35C.

Pathogen & pest resistance: To date, plants of the new *Calibrachoa* have not been observed to be resistant to pathogens and pests common to *Calibrachoa* plants.

It is claimed:

1. A new and distinct *Calibrachoa* plant named 'WNCALSBDBLWH24' as illustrated and described.

* * * * *